United States Patent [19]
Pfisterer et al.

[11] Patent Number: 4,881,031
[45] Date of Patent: Nov. 14, 1989

[54] EDDY CURRENT METHOD AND APPARATUS FOR DETERMINING STRUCTURAL DEFECTS IN A METAL OBJECT WITHOUT REMOVING SURFACE FILMS OR COATINGS

[75] Inventors: Helmut Pfisterer, Essen; Wolfgang Schütze, Oberhausen; Heinz Wezel, Reutlingen, all of Fed. Rep. of Germany

[73] Assignee: Institut Dr. Friedrich Forster Pruferatebau GmbH, Reutlingen, Fed. Rep. of Germany

[21] Appl. No.: 207,664

[22] Filed: Jun. 16, 1988

[30] Foreign Application Priority Data

Jun. 23, 1987 [DE] Fed. Rep. of Germany ....... 3720686

[51] Int. Cl.$^4$ ...................... G01N 27/90; G01R 33/12
[52] U.S. Cl. .................................... 324/233; 324/230; 324/241

[58] Field of Search ............................. 324/228–234, 324/236–242

[56] References Cited

U.S. PATENT DOCUMENTS

| | | | |
|---|---|---|---|
| 3,405,354 | 10/1968 | Callan et al. | 324/233 |
| 3,895,290 | 7/1975 | Audenard et al. | 324/233 |
| 3,904,957 | 9/1975 | Griese | 324/233 |
| 4,564,809 | 1/1986 | Huschelrath et al. | 324/233 X |
| 4,628,260 | 12/1986 | Kimoto et al. | 324/233 X |
| 4,652,823 | 3/1987 | Sutton | 324/233 |
| 4,799,011 | 1/1989 | Muller | 324/233 |

Primary Examiner—Gerard R. Strecker
Attorney, Agent, or Firm—George J. Netter

[57] ABSTRACT

In eddy current testing of coated metal objects for corrosion, test values are arranged into fields corresponding to metal object and coating characteristics permitting direct readout of corrosion existence underneath coating without requiring coating removal.

5 Claims, 3 Drawing Sheets

EDDY CURRENT METHOD AND APPARATUS FOR DETERMINING STRUCTURAL DEFECTS IN A METAL OBJECT WITHOUT REMOVING SURFACE FILMS OR COATINGS

The present invention relates generally to nondestructive testing of metal objects, and, more particularly, to the testing of metal objects for corrosion damage without having to remove surface coatings or films.

BACKGROUND

Many metal objects and products, such as an automotive vehicle, for example, are subject to corrosion damage and it is desirable to be able to test for the nature and extent of such damage without destroying or impairing the item. Automotive vehicles are subject to supervision and testing of load-bearing parts of the vehicles for corrosion damage are performed periodically by such groups as the German Technical Supervisory Boards. Damages of this kind are in most cases either completely invisible or hard to detect, because they are hidden under protective layers such as paint or corrosion-protection layers, or by dirt. When performing the investigation in the past, scrapers and hammers were used to remove the covering layer so that the surface of the bearing layer was exposed for visual inspection. Light hammer strikes or pressure exerted with a scraper tip allow, to a certain degree, evaluation of the remaining load bearing capability of the investigated sections by an experienced inspector.

From patent application GB No. 2 108 672, a device for detecting previously repaired spots in the sheet steel of vehicle bodies is known. The device consists of a Hall transducer and a magnet mounted so that the magnetic flux of the magnet passes through the transducer into the sheet steel of the vehicle body. Three different light signals, controlled by different levels of the transducer signal voltage indicate (1) whether the sheet steel is separated from the transducer only by a thin paint layer, (2) whether an additional filler layer of non-magnetic material has been applied, and (3) whether there is no ferromagnetic material under the transducer or it is spaced from the transducer by a thick filler layer. Although a device of this kind might be helpful for the mentioned special application, it is generally insufficient, as it delivers information only on the distance between transducer and ferromagnetic material, not, however, on the physical conditions of the latter.

In published German patent application DE-OS No. 2 943 584, a device is described for detecting irregularities of a metal base layer covered by a non-metal cover layer. It operates with an eddy-current sensor placed on the cover layer, the sensor responding on distance variations of the metal base layer. A coil integrated into the sensor forms together with a capacitor a parallel-resonant circuit connected to an oscillator. Reactions of eddy currents in the metal base layer with the coil determine the amplitude of the oscillator voltage. The stronger these reactions are, the smaller the distance is between the coil and base layer. The oscillator voltage accordingly can be considered as a measure of this distance, and can be indicated by a measurement device or, in connection with threshhold switches, by optical signals.

As compared to the unit described previously, the latter patented device has the advantage that it can be used to make measurements even with non-ferromagnetic metals. The disadvantage mentioned in regard to the first described device that, except for the distance to the base layer, no information is obtained, applies here, also.

SUMMARY OF THE DISCLOSURE

The present invention provides a method for obtaining information, not only on the distance between a coil probe and a metal layer, but also on material properties of the metal layer.

A series of investigations was necessary for the solution according to the invention. The original assumption that the evaluation of the complex signal voltage offers a possibility for separating the material properties of the metal layer from the distance measurement has been confirmed. It was found out, too, that the separation can be performed within the complex voltage graph with a predetermined frequency excitation signal in a direction extending at an obtuse angle or nearly vertically to the distance direction formerly used exclusively. This permits an effective separation of signals. According to a particularly advantageous embodiment of the invention, take-off curves of sections having specific material properties are used as separating lines of adjacent indication fields.

DESCRIPTION OF A PREFERRED EMBODIMENT

Figure 1:
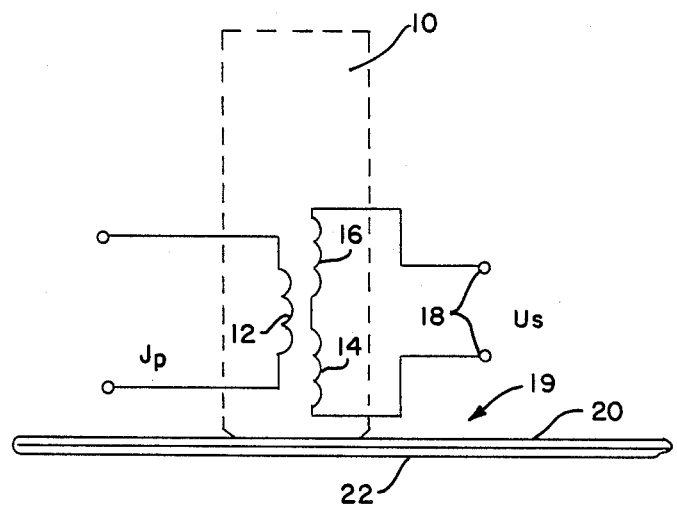
FIG. 1 depicts a coil probe arrangement with respect to a test object.

In FIG. 1 the basic construction of an eddy-current coil probe 10 is represented which can be used in the present invention. It is a transformer-type transducer connected in differentiating manner on the secondary side. Other types of transducers can, however, also be used for the application according to the invention.

The coil probe 10 has, beside a primary winding 12, two secondary windings 14, 16 with an identical number of turns, disposed symmetrically to the primary winding 12 and serially opposed to one another. In case the coil probe 10 is located at a considerable distance from conductive or ferromagnetic objects, a current Jp through the primary winding 12 induces in the two secondary windings 14, 16 equal voltages compensating each other, such that at the terminals 18, a zero output voltage results. If, however, the coil probe 10 is placed on the surface of a metal object 19 to be investigated, in the present case a steel sheet 22 covered with a paint layer 20, the lines of force of the magnetic field induced by the primary coil current Jp penetrate the sheet 22 and generate eddy currents in it. The eddy currents, in turn, induce, because of the different distances to the secondary windings 14, 16, different voltages in the windings, such that at the terminals 18 of the secondary winding 14, 16, a signal voltage Us different from zero results. For the investigations described in the following, a measuring frequency of 30 kHz was used.

Figure 2:
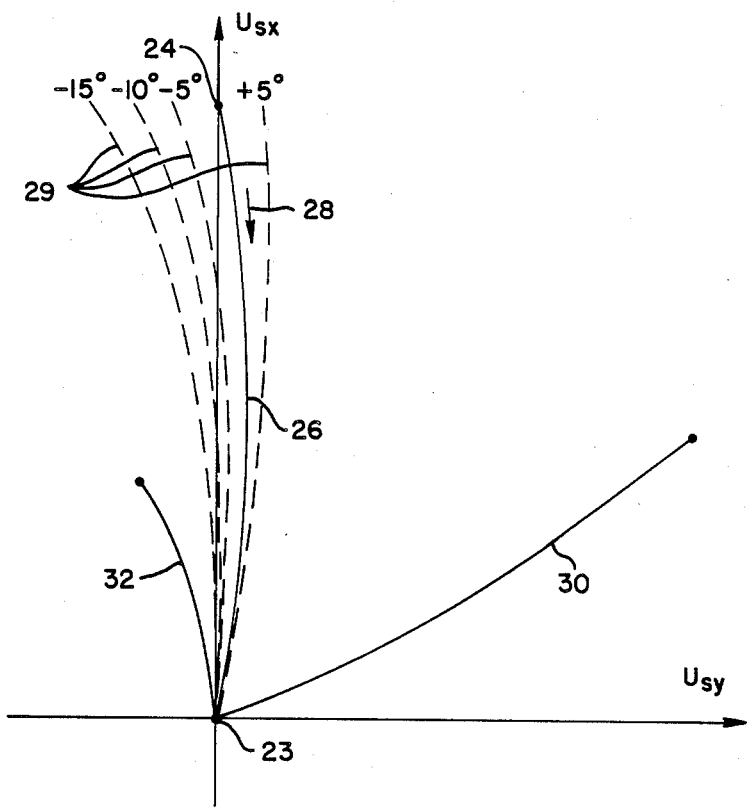
FIG. 2 is a graph of a section of complex test signal.

In FIG. 2, a graph of the signal voltage Us is shown with the two components Usx and Usy as coordinates, the origin 23 of the coordinates corresponding to zero signal voltage existing at the terminals 18. With a coil probe 10 placed on a bare section of sheet steel, the end of the signal voltage vector is at point 24. If the coil probe 10 is held spaced from the metal surface, or it is located on paint layers 20 covering the steel sheets which are progressively thicker, the end of the signal voltage vector moves down from point 24 along curve 26 in the direction of arrow 28 and reaches, finally, with sufficiently large distance between coil probe 10 and sheet steel, the origin 23. This curve is referred to herein as the "take-off curve".

In a first series of investigations, measurements were taken on twelve (12) uncorroded metal sheets, for each of 200 motor vehicles of different manufacturers, types and years of manufacture. It was found out that, except for those equipped with hot-galvanized sheet steel, practically all measurement points are arranged in immediate proximity to curve 26. For better grouping of the measurement points, tolerance areas have been set up by means of separating lines 29 corresponding to take-off curves and spaced apart by angles of 5° with respect to each other. 97.25% of all measurement points lay within the separating lines of ±5°; 2.71% of the measurement points between the separating lines of −5° and −10°; and only 0.04% between the separating lines of +5° and +10°.

In a subsequent series of investigations, measurements were made on 60 metal areas of motor vehicles, for which, based on visual inspections, there was a suspicion of corrosion. Then, the respective metal areas were tested using the conventional methods with scraper and hammer. Here, two fundamentally different kinds of behavior have been detected. If, during a repair operation on fully rusted-through positions, a non-ferromagnetic metal sheet (e.g., aluminum) was inserted, or if, for repair purposes, the steel sheet was processed by tinning material (e.g. 35% tin, 65% lead) applied in the hot state, the respective measurement points for the signal voltage were to be found on the right side of curve 26. For hot-galvanized sheets, the same applies. An example for this behavior is shown by curve 30. On the other hand, however, a corroded steel sheet behaves differently as can be seen, e.g., from curve 32. In this case, the measured values of the signal voltage Us are all found on the left side of curve 26. For relatively light corrosions which are considered satisfactory for load-bearing parts, the tolerance area of measured values is disposed between curve 26 and the line −10°. For heavier corrosions, rust bubbles and rusted through regions, measurement values are clearly and uniformly left of the −10° line.

Furthermore, the thicknesses of protective layers were determined for 250 motor vehicles at 12 different measurement positions, each of which were located on load-bearing members of the vehicle underside. It was found that for 99.9% of all measurements, the layer thickness was less than 3 mm. Further measurements indicated that for this distance of 3 mm, the signal voltage Us is reduced to approximately 15% of the maximum value point 24.

Figure 3:
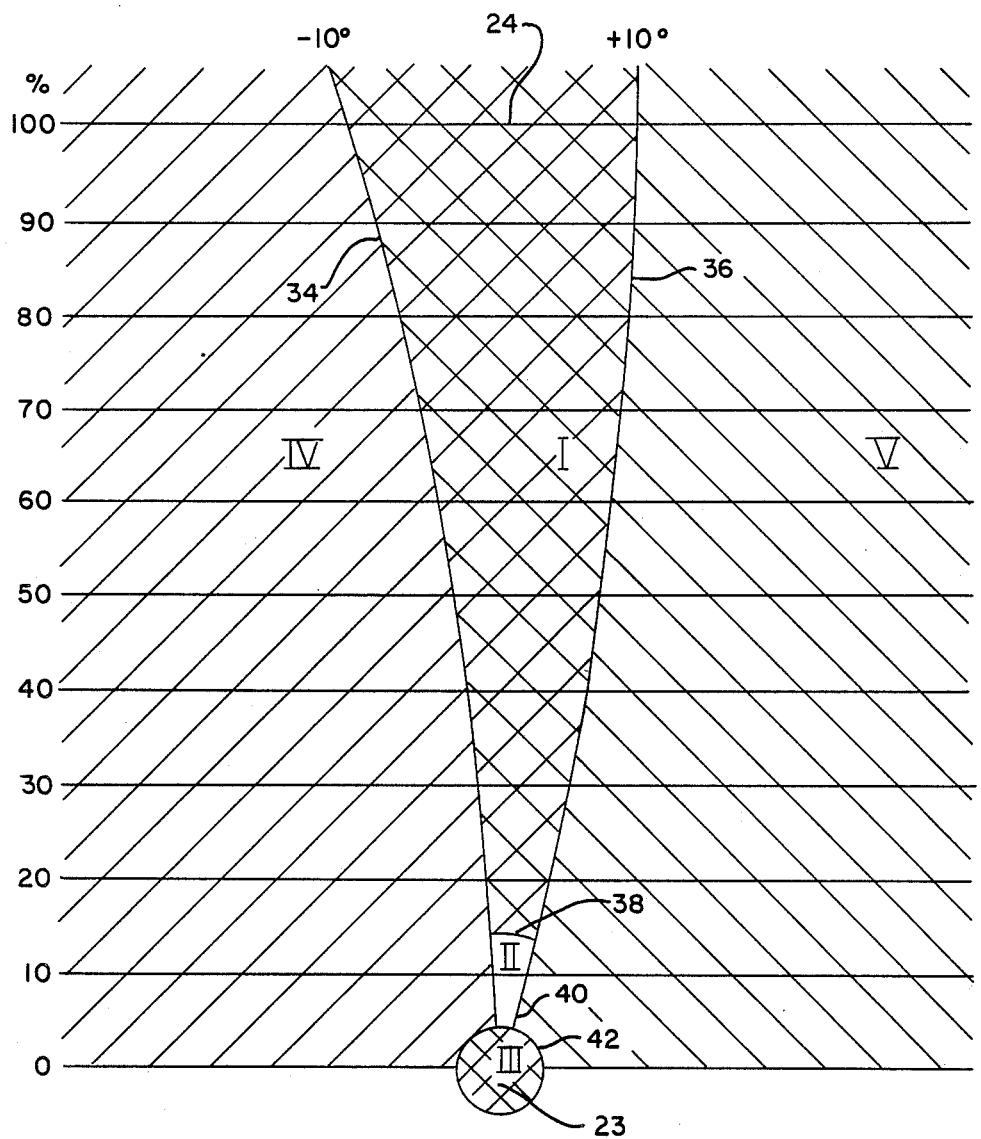
FIG. 3 shows indication fields in the complex signal graph.

It is a fundamental insight of the present invention that based on the foregoing test information, it is possible to perform a subdivision of the complex plane of the signal voltage Us into five indication fields as shown in FIG. 3. Indication field I is limited on the left and on the right by border lines 34 and 36, corresponding to take-off curves at angles of −10° and +10°, and at the bottom by line 38 when the probe is located at a 3 mm spacing from the metal sheet. In field I, therefore, all indications are recorded for non-defective material and for protective layers from 0 to 3 mm. Indication field II is limited at the sides by the border lines 34, 36, at the top by the border line 38, and at the bottom by a border line 40 arranged at a probe to material spacing of 6 mm. In this indication field II, therefore, indications of non-defective material with protective layers between 3 and 6 mm are recorded.

Indication field III is defined by a circular border line 42, with the center at the origin of coordinates 23 and having a radius corresponding to the distance of the border line 40 to the origin of coordinates 23. Indication field III includes all measurements recorded for protective layer thicknesses of more than 6 mm, which thicknesses are not encountered to any great extent in practical applications. Also, in this same indication field, measurements of filler materials of an electrically non-conductive material are to be found.

Indication field IV, the area on the left of border line 34, contains measurements caused by corrosion suspected material. The final indication field V, located to the right of border line 36, includes those measurements based on electrically conductive, non-ferromagnetic foreign material and hot-galvanized sheets.

Figure 4:
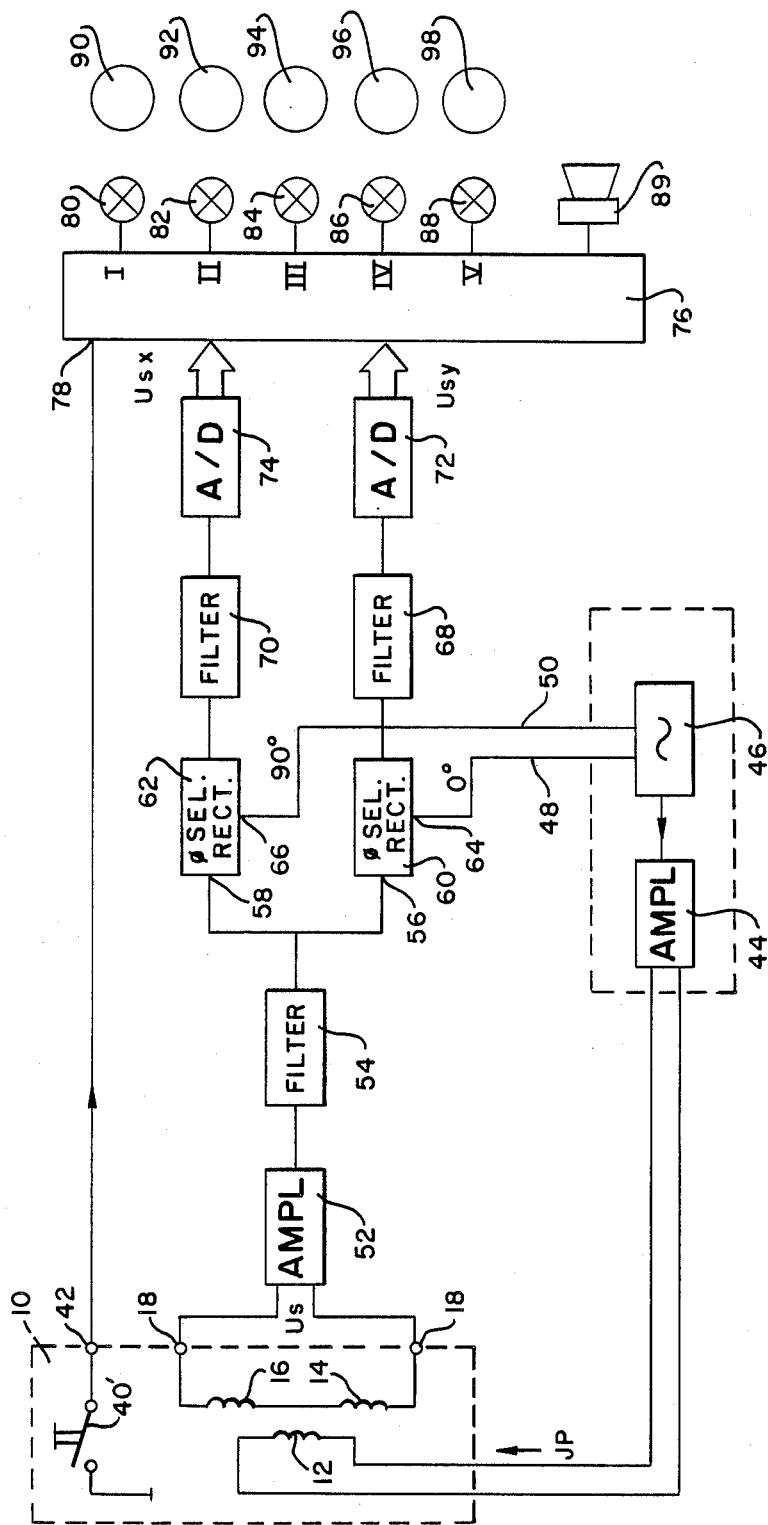
FIG. 4 is a block diagram of a device for carrying out the method according to the invention.

Turning now to FIG. 4, there is a block diagram of a device for carrying out the method according to the invention without the need to represent the complex signal voltage plane on a screen. Coil probe 10 can be identical to that previously described in connection with FIG. 1. In addition, however, a switch 40′ is provided, the position of which signals readiness for measurement and indicating that the coil probe 10 is in sensing position with respect to an object to be investigated. In the simplest case, the switch can be actuated by hand by the person performing the investigations. The switch may, alternatively, be of the kind closing automatically when the probe contacts the object to be investigated. In either case, the signal indicating readiness for measurement is available at an output terminal 42.

The primary winding 12 of the coil probe 10 is fed by a power amplifier 44 which is controlled by an oscillator 46 with a frequency of 30 kHz. The oscillator 46 has additional control signal outputs with the phase relationships 0° and 90° being conducted outside over conductors 48 and 50, respectively.

The signal voltage Us at the terminals 18 of the two secondary windings 14, 16 is connected to the input of a preamplifier 52 and is then conducted from its output over a bandpass filter 54 to the signal inputs 56, 58 of two phase selective rectifiers 60, 62, the control inputs 64, 66 of which are controlled by the 0° and 90° signals from oscillator 46. The output voltages of the phase selective rectifiers 60, 62 are smoothed in lowpass filters 68, 70, outputs of which form the components Usx and Usy of the signal voltage Us and which can be used for the representation of the complex signal voltage graph according to FIG. 2 on the screen of a picture tube.

Instead of producing a video output, the two components Usx and Usy are digitized in two analog/digital converters 72, 74, and are made available to a microprocessor controlled evaluation unit 76 under the control of input 78. The evaluation unit 76, it will be recalled, must be placed in the operative state by actuation of switch 40′. The evaluation unit 76 is provided with a memory means, e.g., a RAM, into which the border lines 34–42 according to FIG. 3 have been previously stored. When the signal indicating readiness for measurement is present at input 78, the complex signal voltage Us in the form of its components Usx and Usy is compared to the stored border lines 34-42. Depending on the result of this comparison, the respective signal voltage is assigned to one of the indication fields I-V. This is indicated by one of the lamps 80-88. An additional acoustic signal can be transmitted by the acoustic signal transmitter 89.

For functional tests, five check or calibration disks 90-98 are provided, each being located close to one of the lamps 80-88. Each check disk has the material physical properties that will test out according to the immediately adjacent lamp 80-88. For example, when the probe 10 is brought near disk 90, the "I" light 80 will be energized, and so forth for the remaining disks 92-98.

We claim:

1. Apparatus for determining the presence of corrosion in a metal object coated with a generally electrically non-conductive material, comprising:
    probe means having a face for being placed on the surface of the metal object, the probe means including an excitation coil, and a pair of receiver coils which are disposed symmetrically to the excitation coil and connected serially opposed to one another, the receiver coils located at different distances from the face;
    an oscillator interconnected with the excitation coil to induce eddy currents in the metal object, said eddy currents inducing a reaction signal in the receiver coils;
    a preamplifier connected across the series connected receiver coils;
    first and second phase selective rectifiers each having an input connected to the preamplifier output;
    said oscillator having two output terminals for providing two control signals of 90 degree phase difference, which terminals are individually connected, respectively, to control the first and second phase selective rectifiers;
    the rectifiers being individually connected to first and second analog to digital convertors; and
    means responsive to the digital output of the analog to digital converters for producing separate identification displays for each of a plurality of ranges of paired digital signals from the first and second converters, into which a complex plane of the digital signals has been divided, each of said paired digital signals defining a point in said complex plane, and one of which ranges represents a metal surface substantially free of corrosion.

2. A method for nondestructively determining the presence of corrosion in an electrically conductive object having its outer surface coated with a non-conductive material by means of a probe having a receiving coil inductively related therewith and face, comprising the steps of:
    inducing eddy currents into the electrically conductive object;
    locating a probe receiving coil adjacent the object by placing the face of the probe on the surface of the object to have a reaction signal inducing in the receiving coil by the eddy currents;
    converting the reaction signal into first and second orthogonal component signals, a pair of such signals defining a point in a complex plane;
    dividing the complex plane into at least three ranges separated from one another by separation lines which are defined by a take-off curve formed by reaction signal values obtained when the probe is located at a bare surface point on the conductive object and at a distant point where reaction signal values are zero, the take-off curves being chosen such that in one range lie only pairs of component signals due to surfaces substantially free of corrosion; and
    displaying an identification of any one of the ranges within which given measured component signals lie.

3. A method as in claim 2, in which further ranges are between two separation lines defined by takeoff curves and above a line corresponding to a first spacing between the probe and the object bare surface point identifying noncorroded object and non-conductive coatings having a thickness ranging from zero to said first spacing;
    between two separation lines defined by take-off curves, beneath the line corresponding to said first spacing and above a line corresponding to a second spacing between the probe and the bare surface of the object, said second spacing being greater than the first spacing; and
    a circular region with center at a spot in the complex plane due to a signal voltage zero when the probe is located distant from the conductive object surface.

4. A method as in claim 2, including the further steps of digitizing the component signals to corresponding digital signals and selecting the appropriate range by a microprocessor prior to displaying an identification of range.

5. A method as in claim 2, in which the eddy currents are induced in the electrically conductive object by a 30 kHz voltage.

* * * * *